US00PP13716P39

(12) United States Plant Patent
Bremner

(10) Patent No.: US PP13,716 P3
(45) Date of Patent: Apr. 8, 2003

(54) GERANIUM PLANT NAMED 'WESTRAY'

(76) Inventor: Alan Heddle Bremner, Bendigo, St. Ola, Kirkwall, Orkney, KW15 1SX, Scotland (GB)

( * ) Notice: Subject to any disclaimer, the term of this patent is extended or adjusted under 35 U.S.C. 154(b) by 7 days.

(21) Appl. No.: 09/834,867

(22) Filed: Apr. 14, 2001

(65) Prior Publication Data

US 2002/0152530 P1 Oct. 17, 2002

(51) Int. Cl.[7] ..... A01H 5/00
(52) U.S. Cl. ..... Plt./324
(58) Field of Search ..... Plt./324

(56) References Cited

U.S. PATENT DOCUMENTS

PP10,474 P * 6/1998 Bloom ..... Plt./324
PP11,252 P * 2/2000 Tyssowski ..... Plt./324
PP12,148 P2 * 10/2001 Van Noort ..... Plt./324
PP12,172 P2 * 10/2001 Dean et al. ..... Plt./324
PP12,175 P2 * 10/2001 Waterer et al. ..... Plt./324

OTHER PUBLICATIONS

UPOV ROM GTITM JOUVE 2002/02 computer database, citation(s) for 'Westray'.*

* cited by examiner

*Primary Examiner*—Bruce R. Campell
*Assistant Examiner*—W C Haas
(74) *Attorney, Agent, or Firm*—Mark P. Bourgeois

(57) ABSTRACT

A new cultivar of *Geranium×cantabrigiense* plant named 'Westray' that is characterized by a dense habit, a profuse and early display of large flowers that may continue blooming sporadically until the end of summer, a flower color that is a stronger, clearer pink, foliage that turns color in fall, and ease of propagation. In combination these traits set 'Westray' apart from all other varieties of Geranium.

2 Drawing Sheets

BOTANICAL CLASSIFICATION

*Geranium×cantabrigiense*

VARIETY DENOMINATION

'Westray'

BACKGROUND OF THE INVENTION

The present invention relates to a new and distinct cultivar of Geranium known botanically as *Geranium×cantabrigiense* and hereinafter referred to by the cultivar name 'Westray'. The new invention is a hybrid between the female parent *Geranium macrorrhizum* 'Lohfelden' (unpatented) and the male parent *Geranium dalmaticum* (unpatented). In 1993 the inventor induced hybridization of *Geranium macrorrhizum* 'Lohfelden' (unpatented) and the species *Geranium dalmaticum* (unpatented). Seeds resulted from this cross, which were then sown in 1994. The inventor selected 'Westray' as a single plant from the resulting seedlings in 1995 in Orkney, Scotland.

'Westray' was bred from a breeding program which was established in 1985. The aim of this breeding program is to produce a range of flower colors of the hybrids between *Geranium macrorrhizum* and *Geranium dalmaticum,* in combination with the dense habit, profuse flowering and general performance exhibited by 'Westray.'

'Westray' is assumed to be sterile and as with all crosses made between the parents, *Geranium macrorrhizum* and *Geranium dalmaticum,* it is female sterile and male sterile. What makes 'Westray' sterile is an incompatibility between its two parent species, which are close enough to provide a first-generation cross but not close enough for that cross to be fertile. It does not produce seed, making it female sterile, and although it produces pollen, the pollen is non-viable, making it male sterile.

The new Geranium plant can be characterized by its dense habit and large, profuse flowers, with a strong, clear pink color, that bloom from March to late June and may continue blooming sporadically into August. The closest comparison varieties are *Geranium dalmaticum* and *Geranium cantabrigiense* 'Cambridge' (unpatented). 'Westray' differs from these in its large flower with a strong, clear pink color and the ability to propagate more readily. 'Westray' is shorter than 'Cambridge' and taller than *Geranium dalmaticum.*

In 1997 the inventor conducted the first asexual propagation in Orkney, Scotland using the method of division. Since that time subsequent asexual propagation has been conducted using vegetative root cuttings, tip cuttings and stem cuttings. Under careful observation successive generations have been determined stable and uniform.

SUMMARY OF THE INVENTION

The following traits have been repeatedly observed and represent the distinguishing characteristics of the new Geranium plant. These traits in combination distinguish 'Westray' from all other varieties of Geranium. The new invention has not been tested under all possible conditions and phenotypic differences may be observed with variations in environmental, climatic, and cultural conditions, however, without any variance in genotype.

1. 'Westray' exhibits a dense habit.
2. 'Westray' exhibits large flowers that are a unique strong, clear pink color.
3. 'Westray' blooms profusely.
4. 'Westray' blooms from March to late June and may continue sporadically into August.

5. 'Westray' propagates easily by stem cuttings, root cuttings, tip cuttings and division.
6. 'Westray' exhibits foliage that turns color in autumn.

BRIEF DESCRIPTION OF THE DRAWINGS

The accompanying color photographs illustrate the distinguishing characteristics of the new cultivar. Sheet 1 shows the plant from a side perspective and illustrates the habit, foliage and profuse blooming of 'Westray'. Sheet 2 is a close-up of the flower, bud and leaf. All photographs are taken using conventional photographic techniques and although colors may appear different from actual colors due to light reflectance, they are as accurate as possible by conventional photography.

BOTANICAL DESCRIPTION OF THE PLANT

The following is a detailed description of the Geranium cultivar named 'Westray'. Data was collected in Arroyo Grande Calif. from plants grown outdoors in one-gallon containers. Color determinations are in accordance with The Royal Horticultural Society Color chart except where general color terms of ordinary dictionary significance are used. The growing requirements are similar to the species and no disease problems have been observed.

Botanical classification: *Geranium×cantabrigiense* 'Westray.'
Parentage: 'Westray' is an induced hybrid resulting from crossing the following plants.
*Female parent.*—*Geranium macrorrhizum* 'Lohfelden' (unpatented).
*Male parent.*—*Geranium dalmaticum (unpatented).*
Common names: Cranesbill and Geranium.
Type: Semi-evergreen perennial.
Use: Border, groundcover or container plant.
Growth: Vigorous grower.
Roots: Fibrous roots.
Growth habit: Creeping, mounding and dense.
Height: 20 cm. in height.
Width: 45 cm. in width.
Branching habit: Basal branching.
Flowering time: Diurnal.
Flowering season: Flowers on the central coast of California in March through late June and may continue sporadically until August. In cooler more temperate regions it may begin blooming later in the year.
Hardiness: USDA Zone 5.
Seasonal interest: A profuse display of large clear-pink flowers and foliage that turns orange-red to yellow-green in autumn.
Propagation method: Propagated by root cuttings, tip cuttings, stem cuttings, and division.
Special needs. Cut back after flowering to induce fresh flush of foliage and flowers.
Soil: Tolerant of a range of soil types, but generally needs moderately fertile, retentive soil.
Light levels: Plant in full sun or part shade.
Crop time: 6–9 months are required to achieve a finished one-gallon container, from a rooted cutting or division.
Rooting time: 2–3 weeks are required for an initial cutting to produce roots.
Stem:
*Stem shape.*—Cylindrical.
*Stem surface.*—Scurfy toward the base and glabrous toward the end.
*Stem color.*—Overall color is a combination of 187A overlaid with 144D, and scurfy areas that are 166B.
*Stem dimensions.*—13 cm. in length by 1 cm. in diameter.
*Secondary stem attachment.*—Sheathing.
*Secondary stem dimensions.*—5 cm. in length by 0.50 cm in width.
*Internode length.*—0.50 cm. to 1 cm. between nodes.
*Color of stipules.*—144D.
*Surface of stipules.*—Glabrous.
*Dimensions of stipules.*—5–6 mm. in length by 2 mm. in width.
*Fragrance.*—Spicily aromatic stems.
Foliage:
*Leaf arrangement.*—Alternate at base, but spirally arranged on remainder of stem.
*Leaf division.*—Palmately divided.
*Leaf shape.*—Compound palmate.
*Leaf base.*—Auriculate.
*Leaf margins.*—Lobed and dentate.
*Leaf apex.*—Mucronulate on each lobe.
*Leaf venation.*—Pinnipalmate.
*Vein color* (*adaxial surface*).—138C.
*Vein color* (*abaxial surface*).—138A.
*Leaf surface* (*adaxial*).—Pubescent.
*Leaf surface* (*abaxial*).—Glabrous.
*Leaf dimensions.*—4–5 cm. in length by 5–7 cm. in width.
*Quantity of leaves.*—Twenty-five or more per stem.
*Young leaf color* (*adaxial surface*).—137A.
*Young leaf color* (*abaxial surface*).—138B.
*Mature leaf color* (*adaxial surface*).—138A.
*Mature leaf color* (*abaxial surface*).—138B.
*Seasonal color changes in leaves.*—Edges turn 183A in autumn. Leaves turn the following colors 19A, 33A and 145A.
*Petiole surface.*—Short, fine hairs toward end nearing leaf and glabrate midway to base.
*Dimensions of petiole.*—2–10 cm. in length and 2 mm. in width.
*Color of petiole.*—Predominant color is 144A with changes in autumn to colors 151A and 183A.
*Foliar fragrance.*—Spicily aromatic leaves.
Flower:
*Shape.*—Rotate.
*Habit.*—Diffuse.
*Form.*—Umbel.
*Quantity.*—Floriferous,producing approximately 6–12 flowers per stem.
*Fragrance.*—None observed.
*Sexuality.*—Sterile.
*Aspect.*—Facing outward and horizontally.
*Flower dimensions.*—2.9 cm in diameter.
*Self-cleaning or persistent.*—Self-cleaning.
*Dimensions of peduncle.*—10–20 cm. in length and 2 mm. in width.
*Peduncle color.*—174A.
*Calyx form.*—Inflated.
*Calyx color.*—147C with streaks of 155A.
*Calyx dimensions.*—Approximately 3–4 mm. in width and 3–4 mm. in length.
*Number of sepals.*—Five in number.
*Petals.*—Five in number.
*Dimensions of petal.*—Approximately 1.5 cm. in length and 1 cm. in width.
*Fused or unfused.*—Petals are unfused.

*Petal color* (*newly opened*).—74B, C.
*Petal color* (*mature*).—66C.
*Petal surface.*—Smooth.
*Bud color.*—67B.
*Bud dimensions.*—5–6 mm. in length and 5–6 mm. in width.
*Bud shape.*—Globose.

Reproductive organs:

*Stamens.*—Ten stamens of equal length in 2 whorls.
*Stamen color.*—74A.
*Stamen dimensions.*—12 mm. in length and 0.50 mm. in width.
*Anther.*—Versatile with two rows.
*Anther dimensions.*—3 mm. in length and 1 mm. in width.
*Shape of anther.*—Oblong in shape.
*Color of anther.*—61A.
*Pollen color.*—13 C.
*Quantity of pollen.*—Low and non-viable.
*Pistil dimensions.*—18 mm. in length and 0.50 mm. in width.
*Pistil color.*—74 C.
*Pistil shape.*—Slender like a filament.
*Stigma dimensions.*—1 mm. in length and 1 mm. in width.
*Stigma shape.*—Diverges into four sections at apex.
*Stigma color.*—74A.
*Style dimensions.*—1.5 cm. in length and 0.50 mm. in width.
*Style color.*—74C.
*Style shape.*—Slender like a filament.
*Ovary position.*—Superior.
*Ovary color.*—157D.
*Ovary dimensions.*—2.5 mm. in width and 3 mm. in height.

Seed:

*Assumed to be sterile.*—No seed has been observed by the inventor.

What is claimed is:

1. A new and distinct variety of Geranium plant named 'Westray' as described and illustrated herein.

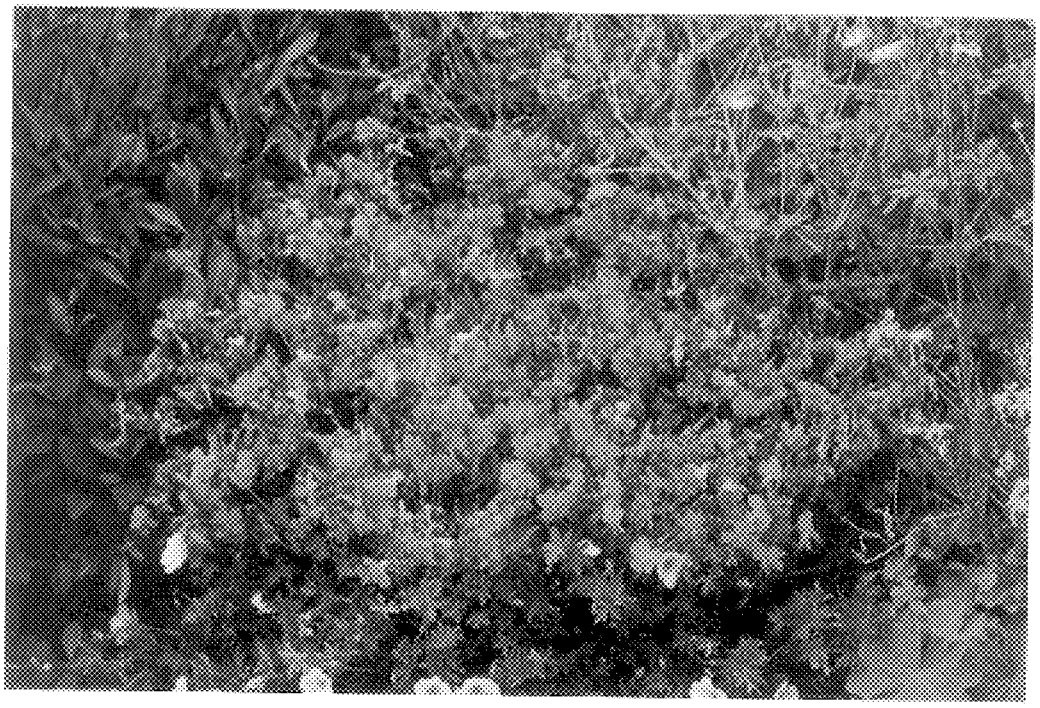

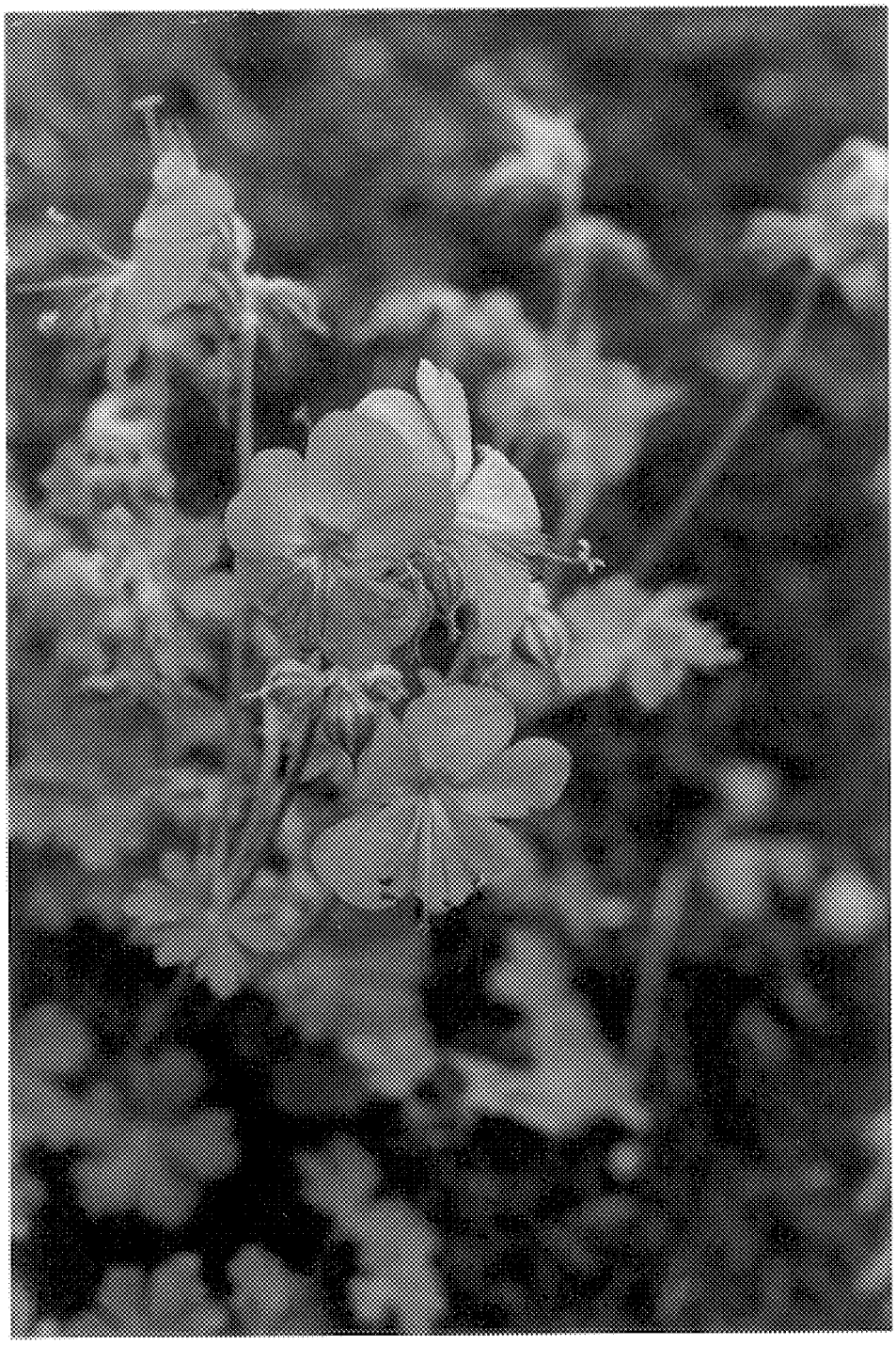

* * * * *